(12) United States Patent
Neethirajan et al.

(10) Patent No.: US 9,316,591 B1
(45) Date of Patent: Apr. 19, 2016

(54) BIOSENSOR FOR DETECTION OF SUBCLINICAL KETOSIS

(71) Applicants: Suresh Neethirajan, Guelph (CA); Xuan Weng, Guelph (CA); Longyan Chen, Guelph (CA)

(72) Inventors: Suresh Neethirajan, Guelph (CA); Xuan Weng, Guelph (CA); Longyan Chen, Guelph (CA)

(73) Assignee: University of Guelph, Guelph, Ontario (CA)

( * ) Notice: Subject to any disclaimer, the term of this patent is extended or adjusted under 35 U.S.C. 154(b) by 0 days.

(21) Appl. No.: 14/617,346

(22) Filed: Feb. 9, 2015

(51) Int. Cl.
  *G01N 21/00* (2006.01)
  *G01N 21/77* (2006.01)
  *G01N 33/50* (2006.01)

(52) U.S. Cl.
  CPC ............... *G01N 21/77* (2013.01); *G01N 33/50* (2013.01); *G01N 2021/7786* (2013.01)

(58) Field of Classification Search
  CPC .......... G01N 2800/52; G01N 33/6893; G01N 2800/56; G01N 2800/042; G01N 2800/50; G01N 2800/044; G01N 2800/32; G01N 33/5091; G01N 2560/00; G01N 2800/04; G01N 33/483; G01N 33/487; G01N 2570/00
  See application file for complete search history.

(56) References Cited

U.S. PATENT DOCUMENTS

| 2008/0085550 | A1* | 4/2008 | Werner | G01N 15/1475 435/287.2 |
| 2008/0158543 | A1* | 7/2008 | Puskas | G01N 21/6428 356/36 |
| 2009/0042310 | A1* | 2/2009 | Ward | G01N 15/1404 436/154 |
| 2009/0161100 | A1* | 6/2009 | Minot | G02B 21/34 356/244 |
| 2009/0170149 | A1* | 7/2009 | Viator | G01N 21/1702 435/29 |
| 2013/0180868 | A1* | 7/2013 | Huang | G01N 33/64 205/782 |

* cited by examiner

*Primary Examiner* — Michael P Stafira
(74) *Attorney, Agent, or Firm* — Joseph Stecewycz (57) ABSTRACT

A method of detecting subclinical ketosis in a dairy animal comprises the steps of: obtaining a sample from the dairy animal, the sample containing one of a serum sample or a milk sample; incubating a mixture of the sample and a reactant containing $NAD^+$-functionalized quantum dots to produce an incubated mixture; irradiating the incubated mixture with optical radiation of a first wavelength so as to emit fluorescent radiation of a second wavelength from the incubated mixture; irradiating a photodetector with the fluorescent radiation so as to generate an electrical signal; and performing data acquisition using the photodetector electrical signal to determine a BHBA concentration for the sample.

13 Claims, 8 Drawing Sheets

BIOSENSOR FOR DETECTION OF SUBCLINICAL KETOSIS

FIELD OF THE INVENTION

The present invention relates to a system and method of detecting subclinical ketosis (SCK) and, in particular, to a method of SCK detection in dairy animals.

BACKGROUND OF THE INVENTION

It has been known in the art for some years that when the modern dairy cow transitions from a non-lactating state to a lactating state during the periparturient period, she undergoes tremendous physiological challenges resulting in an overall state of immune suppression. These changes are characterized by inflammatory conditions, susceptibility to metabolic disorders, uterine and mammary infections, and loss of appetite. These stresses are further complicated by the fact that the sudden initiation of an increase in milk production means that the animal is metabolically in a state of negative energy balance during the immediate postpartum period (approximately eight to ten weeks).

Many of the stress symptoms that individual cows experience go unnoticed. Not only are the animals' health and welfare compromised, but there are also significant economic implications. These animals will have difficulty conceiving, thereby exacerbating losses. To have reliable biomarkers of inflammatory and health status that can be routinely measured is of critical importance to detect, intervene, and manage at-risk cows as early as possible. Subclinical ketosis (SCK) is defined as elevated concentrations of circulating ketone bodies in the absence of clinical signs.

SCK has been found to be associated with high risk of clinical ketosis and displaced abomasum. In addition, subclinically affected cows appear to have reduced milk production than those with normal ketone body concentrations. The economic losses caused by SCK may be huge due to the treatment costs, decreased milk yield and decreased reproductive efficiency. An estimated 40 to 60 percent of cows in North America dairy herds are affected by early lactational incidence of SCK, which is much higher than the two to fifteen percent incidence with clinical ketosis.

Determination of β-hydroxybutyrate (BHBA) is considered as the golden standard to diagnose subclinical ketosis. Cows with BHBA in their blood, milk, and urine typically experience a period of negative energy balance. The detection of ketosis clinical signs varies, but blood BHBA concentration of 1.2~2.9 has been used as the upper threshold for SCK.

Early detection of SCK by measurement of BHBA concentration will help farmers, as these diseases generally have a poor prognosis for production and survival. BHBA in cows' blood and milk are commonly used to diagnose SCK. Monitoring blood BHBA is superior to monitoring urine due to its stability. At present, such tests may be determined spectrophotometrically by traditional clinical laboratory means, and would require the producer to send samples to a lab and wait for the results, a process which is inconvenient and expensive. The advantage of detecting blood BHBA is that no rigorous sample handling precautions are required during the specimen transportation due to the reasonable stability of BHBA in blood.

One obvious advantage of using milk instead of blood for analysis of ketosis is the noninvasive nature of milk sampling. However, because of its nontransparent nature, opacity of the sample is incompatible with spectrophotometry. Consequently, milk needs extensive pretreatment when using traditional analytical methods, typically, precipitation, centrifugation, and special harvesting are necessary. Current cow-side milk testing techniques for BHBA are not accurate and only semi-quantitative results are obtained.

What is needed is a reliable method of SCK detection that can be conducted on-site using serum samples or milk samples.

BRIEF SUMMARY OF THE INVENTION

In one aspect of the present invention, method of detecting subclinical ketosis in a dairy animal comprises the steps of: obtaining a sample from the dairy animal, the sample containing one of a serum sample or a milk sample; incubating a mixture of the sample and a reactant containing $NAD^+$-functionalized quantum dots to produce an incubated mixture; irradiating the incubated mixture with optical radiation of a first wavelength so as to emit fluorescent radiation of a second wavelength from the incubated mixture; irradiating a photodetector with the fluorescent radiation so as to generate an electrical signal; and performing data acquisition using the photodetector electrical signal to determine a BHBA concentration for the sample.

In another aspect of the present invention, a method of detecting subclinical ketosis using a sample from a dairy animal comprises the steps of: preparing a reactant containing $NAD^+$-functionalized quantum dots by modifying a plurality of carboxyl group capped quantum dot nanoparticles with 3-aminophenyl boronic acid (APBA) with a carbodiimide reaction; incubating the reactant with the sample to produce an incubated mixture; irradiating the incubated mixture with 470 nm optical radiation; irradiating a photodetector with fluorescent radiation emitted from the incubated mixture so as to generate an electrical signal; and performing data acquisition on the electrical signal to determine a BHBA concentration for the sample.

In still another aspect of the present invention, a biosensor system suitable for detecting subclinical ketosis (SCK) in a subject animal from a sample of blood serum or milk obtained from the subject animal, the system comprising: a reactant containing a plurality of nicotinamide adenine dinucleotide ($NAD^+$)-functionalized quantum dots; a microfluidic chip having a sensing well for receiving an assay mixture of the sample and the reactant; an optical sensor assembly having an optical radiation source for inducing fluorescent radiation in the assay mixture, and an optical detector for producing an electrical signal in response to the fluorescent radiation; and at least one of a microcontroller board, a computer, and a mobile communication device for receiving the electrical signal and performing data acquisition to determine the amount of β-hydroxybutyrate (BHBA) in the sample.

The additional features and advantage of the disclosed invention is set forth in the detailed description which follows, and will be apparent to those skilled in the art from the description or recognized by practicing the invention as described, together with the claims and appended drawings.

BRIEF DESCRIPTIONS OF THE DRAWINGS

The foregoing aspects, uses, and advantages of the present invention will be more fully appreciated as the same becomes better understood from the following detailed description of the present invention when viewed in conjunction with the accompanying figures, in which.

DETAILED DESCRIPTION OF THE INVENTION

The present invention relates generally to the point-of-care sensitive detection of BHBA in serum and milk samples using a sensitive microfluidic biosensor. The following detailed description is of the best currently contemplated modes of carrying out the invention. The description is not to be taken in a limiting sense, but is made merely for the purpose of illustrating the general principles of the invention.

Early detection of health issues allows the producer or veterinarian to intervene before the animals' production levels, or even survival, is threatened. Increased concentrations of β-hydroxybutyrate (BHBA), a key indicator for diagnosis of subclinical ketosis (SCK), indicate health stress in cows well before any external symptoms are observable. The present invention uses quantum dots (QDs) functionalized with cofactor nicotinamide adenine dinucleotide (NAD) prepared for a sensing event. QDs are semiconductor nanocrystals possessing unique optical properties due to quantum confinement effects. A fluorescence analysis is performed on functionalized QDs in prepared samples to determine BHBA concentration.

Properties such as sharp emission spectra, broad absorption spectra, higher quantum yields, and tunable emission frequencies make QDs excellent fluorescence labels for Förster resonance energy transfer (FRET) or electron transfer (ET) processes-based applications. The disclosed method of using functionalized QDs is superior to the conventional methods using organic dyes, as functionalized QDs provide a brighter, narrower emission, along with higher quantum yield and longer lifetime. Standard BHBA solution, BHBA in milk, and blood samples from cows can be successfully measured by the disclosed novel technology, achieving a detection limit at a level of approximately 10 μM.

Microfluidics is an emerging technology that provides new approaches for detection of toxins in food supplies and has been widely used in biosensor applications, which are mainly used to enhance analytical performance by miniaturization. Microfluidic biosensors present distinctive advantages such as significantly increasing sensitivity, reducing assay time, and sample/reagent consumptions. In the present invention, BHBA detection is performed on a novel microfluidic platform that combines low cost and a miniaturized optical sensor assembly.

The disclosed integration of the microfluidic biochips and QD fluorescence provides for capitalizing on benefits such as low analyte volume, portability, low detection limit, and superior sensitivity and specificity. It can be appreciated by one skilled in the art that quantitative detection capabilities for identification and detection of chemical species and biomarkers through the integration of a portable optical biosensor with a microfluidic biochip will lead to the next generation of diagnostic devices, and open up future applications.

Figure 1:
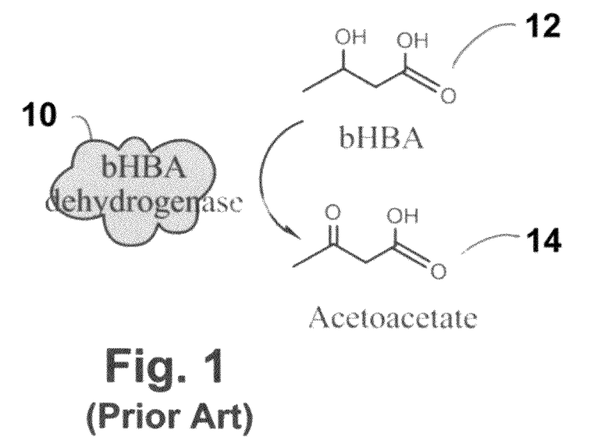
FIG. 1 is a diagrammatical illustration of enzymatic catalysis of BHBA to acetoacetate, in accordance with the present state of the art.
Figure 2:
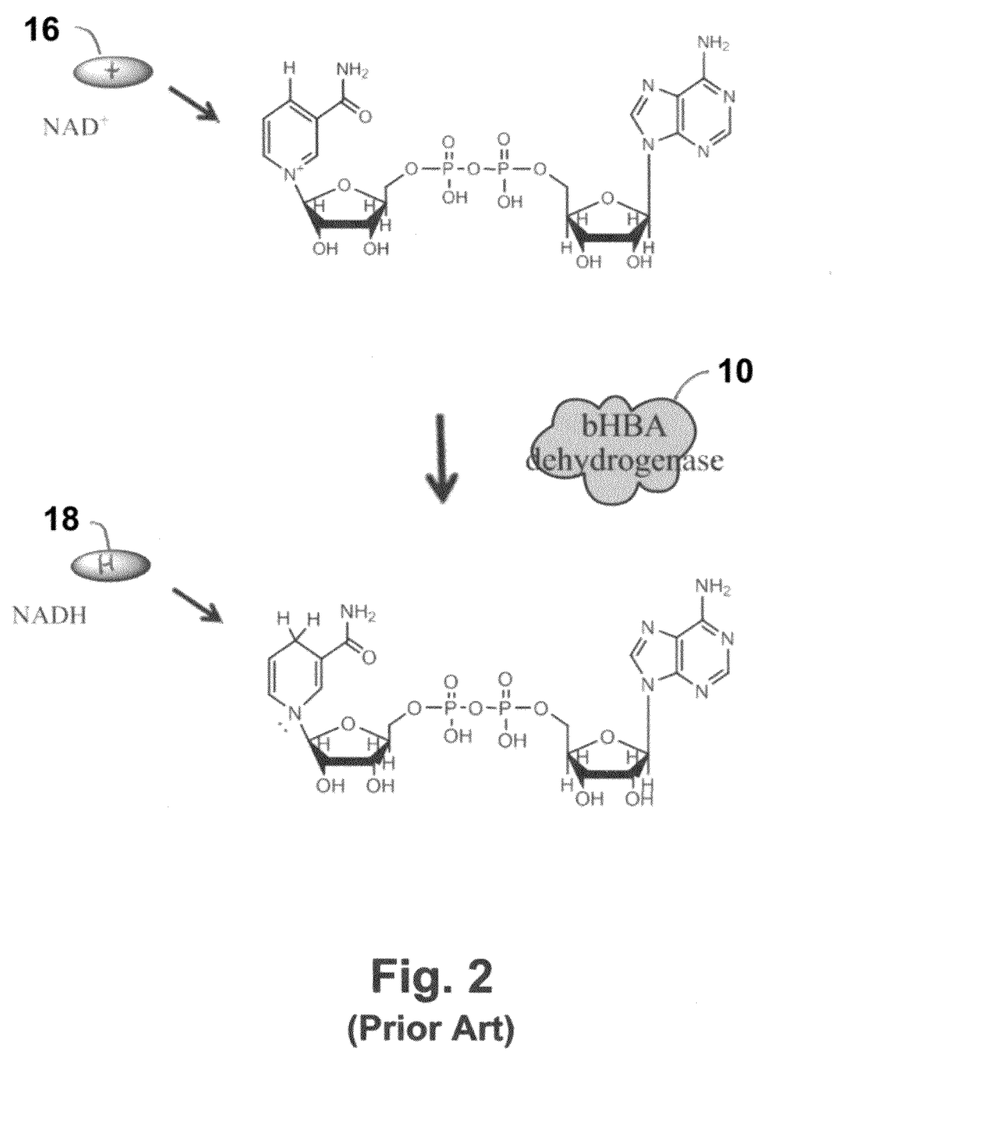
FIG. 2 is a diagrammatical illustration of the conversion by the enzyme BHBA dehydrogenase of nicotinamide adenine dinucleotide to its reduced form β-nicotinamide adenine dinucleotide, in accordance with the present state of the art.

As shown in FIG. 1, the disclosed biosensor operation is based on the enzymatic catalysis of BHBA 12 to acetoacetate 14 with BHBA dehydrogenase 10. The enzyme BHBA dehydrogenase 10 concomitantly converts cofactor nicotinamide adenine dinucleotide (NAD$^+$) 16 to its reduced form β-nicotinamide adenine dinucleotide (NADH) 18, as shown in FIG. 2.

Figure 3:
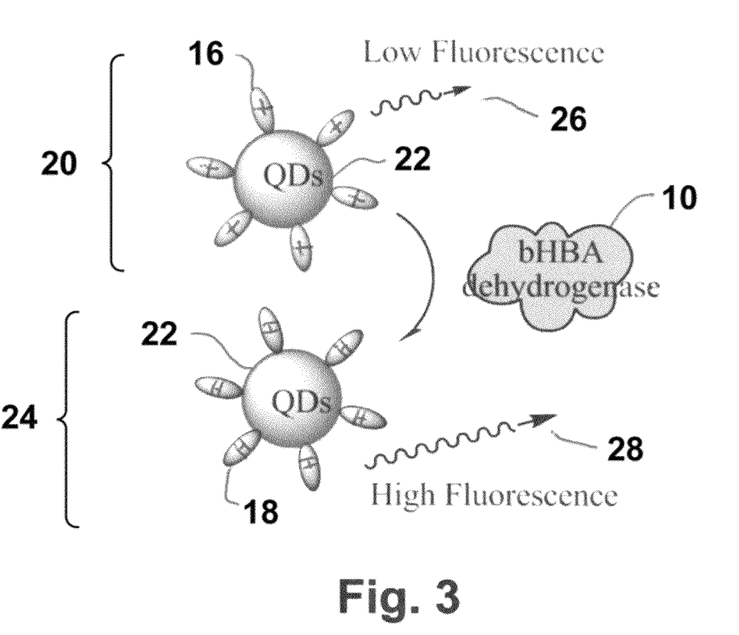
FIG. 3 is a diagrammatical illustration of the use of BHBA dehydrogenase to convert conjugated nicotinamide adenine dinucleotides in NAD$^+$-functionalized quantum dots to their reduced form β-nicotinamide adenine dinucleotide, in accordance with an aspect of the present invention.

In accordance with an exemplary embodiment, NAD$^+$ 16 may be pre-conjugated with fluorescent nanoparticle quantum dots (QDs) 22 to produce NAD$^+$-functionalized quantum dots 20, shown in FIG. 3. The compound NAD$^+$ 16 is known to partially quench the fluorescence of the NAD$^+$-functionalized QDs 20 through an energy transfer (ET) process, as indicated by the "Low Fluorescence" radiation 26. By using the enzyme BHBA dehydrogenase 10 to convert the conjugated nicotinamide adenine dinucleotides 16 in the NAD$^+$-functionalized QD 20 to their reduced form β-nicotinamide adenine dinucleotide (NADH) 18, there is produced an NADH-functionalized QD 24.

It is known in the relevant art that the reduced form compound NADH has no significant effect on fluorescence from the QD 24, as indicated by the "High Fluorescence" radiation 28. The change of fluorescent intensity from the cofactor conjugated QD 20 to the reduced form conjugated QD 24 can advantageously be used to indicate the change of BHBA concentration in samples. It has been shown that the compound NADH has better affinity than NAD$^+$ when conjugated onto QDs 22. NADH is also more competitive than NAD$^+$ in an NAD$^+$/NADH mixture because there is a larger intensity difference before and after mixing. These properties of NADH-functionalized QDs make it an ideal fluorescence probe in a BHBA biosensor.

The disclosed biosensor system and method couples: (i) the produced quantity of the reduced form conjugated QDs 24 to indicate the amount of BHBA concentration in samples; (ii) a microfluidic platform to facilitate the reaction in the field, and (iii) an optical detection unit to detect fluorescence from the reduced form conjugated QDs 24, as described in greater detail below. The resulting system is capable of providing rapid and accurate, on-site assay of BHBA concentration from a relatively small amount of milk or serum sample.

Figure 4:
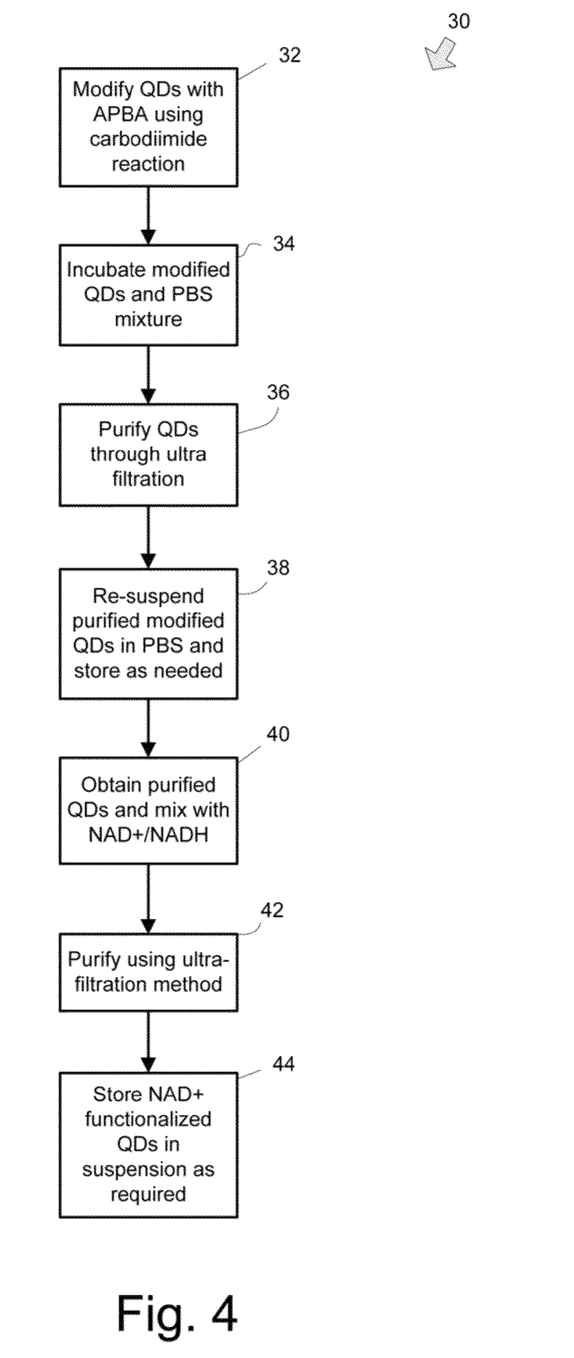
FIG. 4 is a flow chart describing the conversion of conjugated nicotinamide adenine dinucleotides in NAD$^+$-functionalized quantum dots to their reduced form β-nicotinamide adenine dinucleotide, as shown in FIG. 3.

In an exemplary embodiment, NAD$^+$-functionalized QDs 20 and NADH-functionalized QDs 24 can be prepared following steps as described in a flow chart 30, in FIG. 4. Carboxyl quantum dots, such as Qdot® 655 ITK™, can be obtained from Life Technologies of Burlington, ON, Canada. The carboxyl group capped QD nanoparticles 22 can be modified with 3-aminophenyl boronic acid (APBA) through a carbodiimide reaction, at step 32.

In an exemplary embodiment, 50 μl, of 8 μM stock solution of carboxyl QDs 22 are mixed with 50 μL of 10 mg/mL of APBA dispersed in a phosphate buffered saline (PBS) and tetrahydrofuran (THF) 1:1 by volume solution. The resulting mixture is gently shaken for about three minutes. Next, an approximately 25 μL volume of a 10 mg/mL concentration solution of N-(3-dimethylaminopropyl)-N'-ethylcarbodiimide hydrochloride (EDC) is added. The volume of the subsequent mixture can be increased to a volume of approximately one mL with the addition of PBS.

At step 34, the mixture is incubated at room temperature for approximately two hours under gently shaking. At step 36, the QD nanoparticles 22 are preferably purified via ultrafiltration using centrifugal filters such as Amicon Ultra-0.5 mL centrifugal filters available from EMD Millipore Inc. The purified QD nanoparticles 22 are then re-suspended in 1 mL of PBS, at step 38, and can be stored in a dark environment for later use.

For $NAD^+$/NADH conjugation, the purified QDs 22 nanoparticles are further mixed with $NAD^+$/NADH using a feeding molar ratio of APBA-QDs to $NAD^+$/NADH of approximately 1/6000 for about one hour at room temperature, at step 40. The nanoparticles are again purified by ultra-filtration and re-suspended in PBS to final concentration of 0.4 μM, at step 42. The $NAD^+$/NADH-QDs solution may be stored at about 4° C. under dark conditions, at step 44, until required.

The assay process for a serum sample begins with the collection of cow's blood from the coccygeal blood vessels. The sample is placed in a vacuum tube without anticoagulant and stored in a cool place. Within six hours after collection, the blood sample is then centrifuged at 2990 g's at 4° C. to harvest serum, and stored at −20° C. for further use. Before assaying, the serum sample is thawed at room temperature and diluted with PBS buffer to a series of concentration ranging from 10 μM to 1000 μM.

As an alternative to serum sampling, a milk sample may be centrifuged at room temperature at 2300 g's for three minutes, twice, and then the suspension may be removed. Fortified milk sample solutions are prepared by spiking BHBA concentration ranging from 0 to about 1000 μM to the centrifuged milk for further use.

Figure 5:
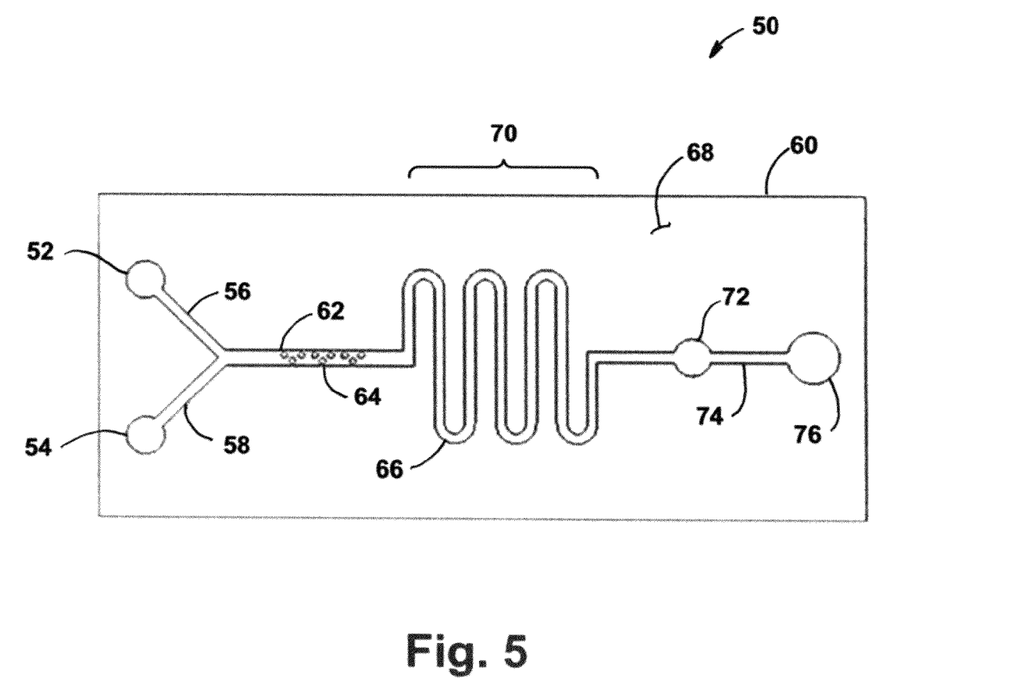
FIG. 5 is a diagrammatical view of a microfluidic chip, in accordance with an aspect of the present invention.

The BHBA concentration in samples may be determined via a fluorescence analysis of the functionalized QDs as may be performed on the surface of a microfluidic chip 50, shown in FIG. 5. It should be understood that the disclosed method can be practiced with conventional equipment, but that the microfluidic chip 50 enables a user to perform the assay process in the field. The microfluidic chip 50 can be fabricated by using conventional methods. In an exemplary embodiment, a silicon wafer master mold is made by forming a photomask on a silicon wafer. A 10:1 mixture of polydimethylsiloxane (PDMS) prepolymer and curing agent, available as Sylgard from Dow Corning, Burlington, ON, Canada, can be applied as a layer on a master mold and cured for about four hours at 75° C. The film of solidified PDMS polymer can be removed from the master mold and becomes a microfluidic chip replica film 68.

One end of the solidified PDMS chip replica film 68 can be punched, or otherwise mechanically modified, so as to form a sample inlet 52 and a reactant inlet 54 in the PDMS chip replica film 68. A product outlet 76 may also be provided by further modifying a distal end of the PDMS chip replica film 68. The resultant PDMS chip replica film 68 may be bonded onto a glass slide 60 to form the microfluidic chip 50. The bonding operation is preferably performed subsequent to an oxygen plasma treatment of the PDMS chip replica film 68 conducted for about forty seconds.

Figure 6:
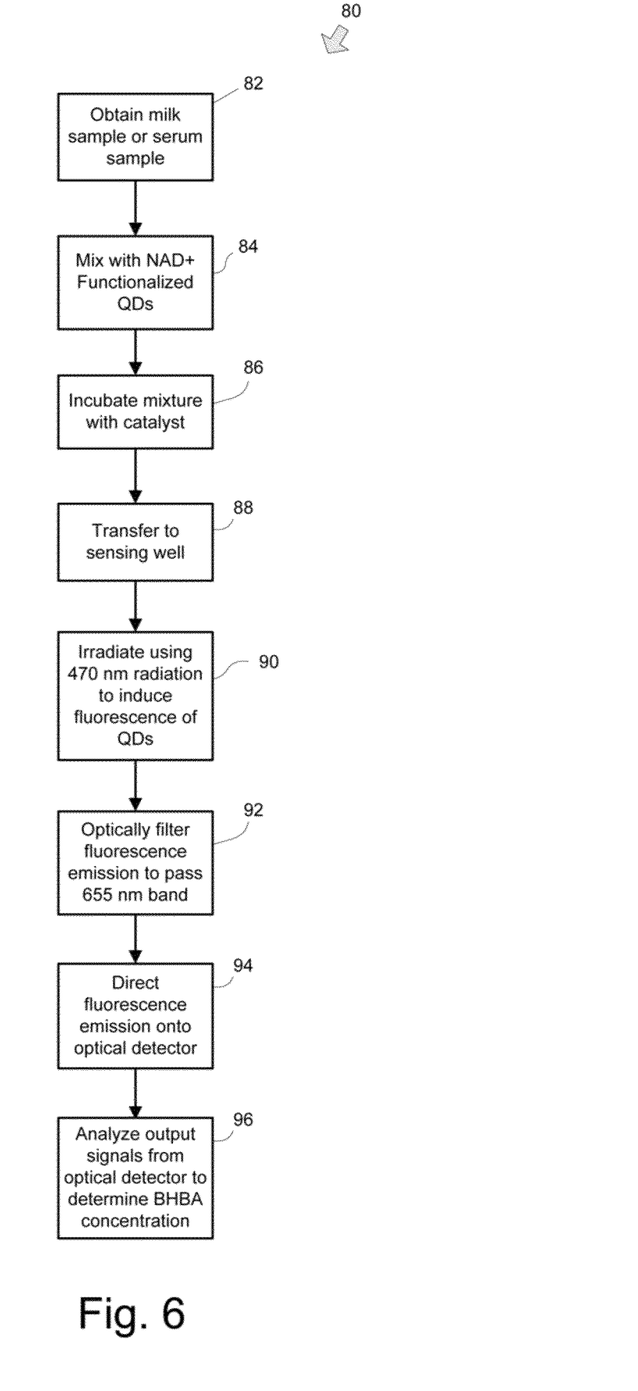
FIG. 6 is a flow diagram describing detection of BHBA using NADH-functionalized quantum dots produced in FIG. 4.

As described above, the disclosed BHBA detection process may be conducted on site by using the microfluidic chip 50, in accordance with a flow diagram 80, shown in FIG. 6. The milk sample or the serum sample is obtained, at step 82. At step 84, the milk sample or the serum sample is mixed with the reactant, that is, the reduced form $NAD^+$-functionalized QDs 24. The milk/serum sample and the $NAD^+$-functionalized QDs 24 reactant can be introduced into the sample inlet 52 and the reactant inlet 54 on the microfluidic chip 50 for combining in the mixing channel 62.

Preferably, the mixing channel 62 contains a plurality of posts 64 disposed in the flow path of the mixing channel 62. The posts 64 function to enhance the mixing effect as the reactants flow through the mixing channel 62 from the first reactant channel 56 and the second reactant channel 58. In an exemplary embodiment, the mixing channel 62 may be approximately 200 μM in width, and the posts 64 may be about 80 μM in diameter. In the configuration shown, the mixed reactants flow from the mixing channel 62 to an incubation region 66 on the microfluidic chip 50.

The incubation region 66 comprises a serpentine incubation channel 68 of a specified width and length. The serpentine incubation channel 68 provides a containment volume sufficiently large as to hold the required amount of the mixed reactants for the incubation process of step 34, above. After the incubation process has been completed, a predetermined amount of the resulting product flows to a sensing well 72, at step 88, for quantitative analysis, as described below. In an exemplary embodiment, the sensing well 72 may be about 2.5 mm in diameter.

The sample in the sensing well 72 is next irradiated with optical radiation having a specified wavelength, the wavelength selected to produce fluorescence in the sample mixture, at step 90. In an exemplary embodiment, the radiation incident on the sample mixture has a wavelength of approximately 470 nm. After the assay has been completed, the product can be removed from the sensing well 72, via an outlet channel 74, to the product outlet 76.

Figure 7:
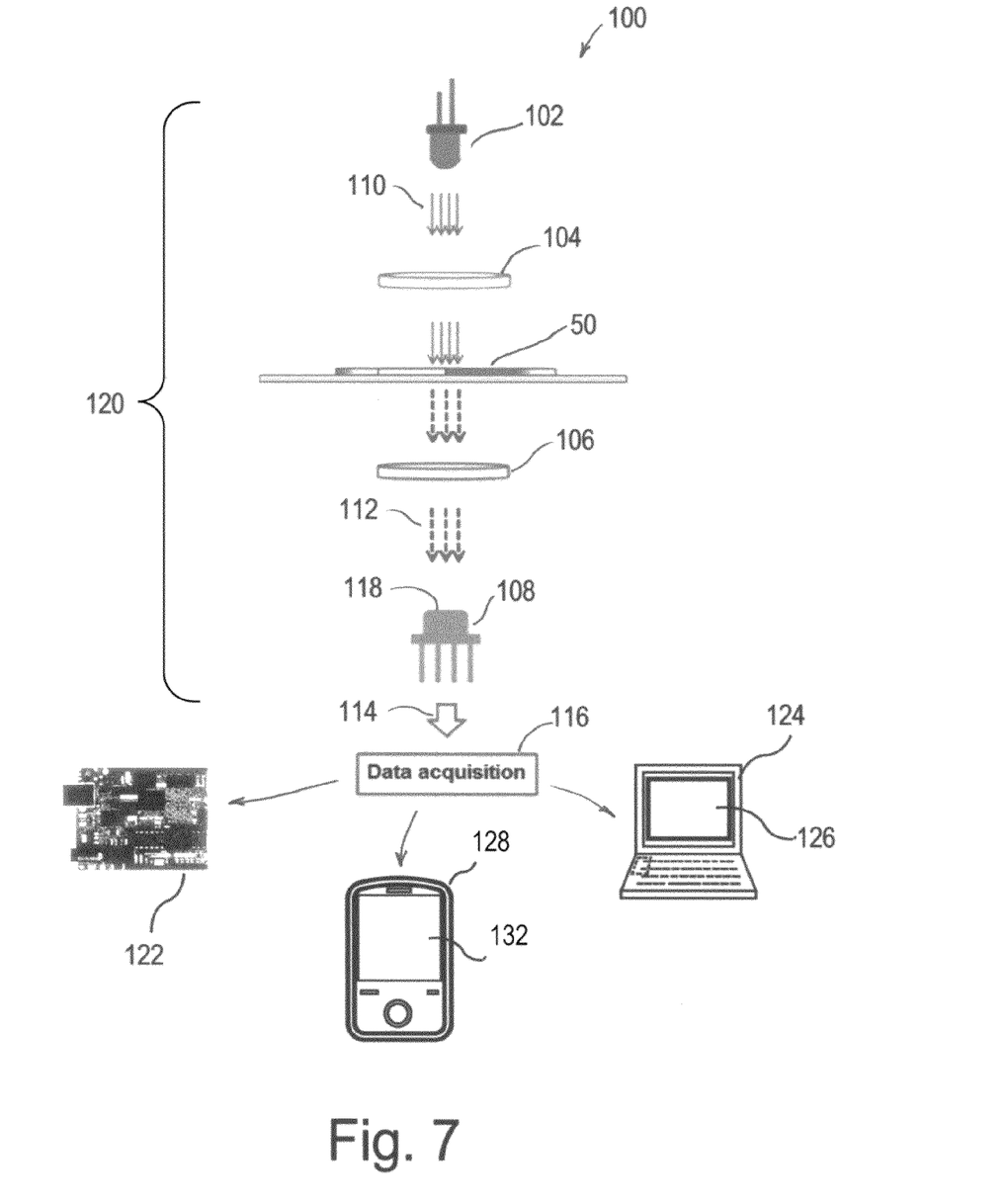
FIG. 7 is a diagrammatical view of a portable optical biosensor assaying a sample in the microfluidic chip of FIG. 5.

There is shown in FIG. 7 an exemplary embodiment of a biosensor system 100 comprising a miniaturized optical sensor assembly 120. The optical sensor assembly 120 suitable for performing fluorescence signal analysis on an assay sample disposed in the sensing well 72 of the microfluidic chip 50, as described in step 90 above. In an exemplary embodiment, the optical sensor assembly 120 comprises a high brightness optical radiation source 102, an optional first single-band bandpass filter 104, a second single-band bandpass filter 106, and a high sensitivity optical radiation detector 108. The first single-band bandpass filter 104 is positioned to avoid possible interference from undesirable radiation wavelengths produced by the optical radiation source 102. Optical radiation 110 emitted from the optical light source 102 is transmitted along an optical path passing through the first single-band bandpass filter 104 and the second single-band bandpass filter 106 to impinge on the optical radiation detector 108. The sensing well 72 of the microfluidic chip 50 is positioned in the optical path of the optical radiation 110, between the first single-band bandpass filter 104 and the second single-band bandpass filter 106.

In an exemplary embodiment, the high brightness optical radiation source 102 may comprise a high brightness light-emitting diode (LED) having an output at a wavelength of 470 nm, such as the Luxeon Rebel LED available from Luxeon Star LEDs of Brantford, ON, Canada. The first single-band bandpass filter 104 preferably has a single-band bandpass at 470 nm, and the second single-band bandpass filter 106 preferably has a single-band bandpass at 655 nm, where both filters 104, 106 may be obtained from Semrock, Inc. of Rochester, N.Y., USA. The optical radiation detector 108 preferably comprises a high sensitivity photodiode, such as available from Hamamatsu of Bridgewater, N.J., USA.

The fluorescence signal 112 that is emitted from the NADH-functionalized QDs 24 produces an electrical output signal 114 from the optical radiation detector 108. In an exemplary embodiment, the output signal 114 may be digitized for a data acquisition module 116, such as a programmable microcontroller 122, similar to the Arduino Uno microcontroller board available from SparkFun Electronics, Niwot, Colo., USA. A position marker (not shown) may be used to facilitate the alignment between the sensing well 72 and a sensing window 118 of the optical radiation detector 108. In an alternative embodiment, the data acquisition module 116 may comprise a personal computer 124 with the analytical results provided on a video display 126, or a personal communication device 128 with the analytical results provided on a screen 132.

Figure 8:
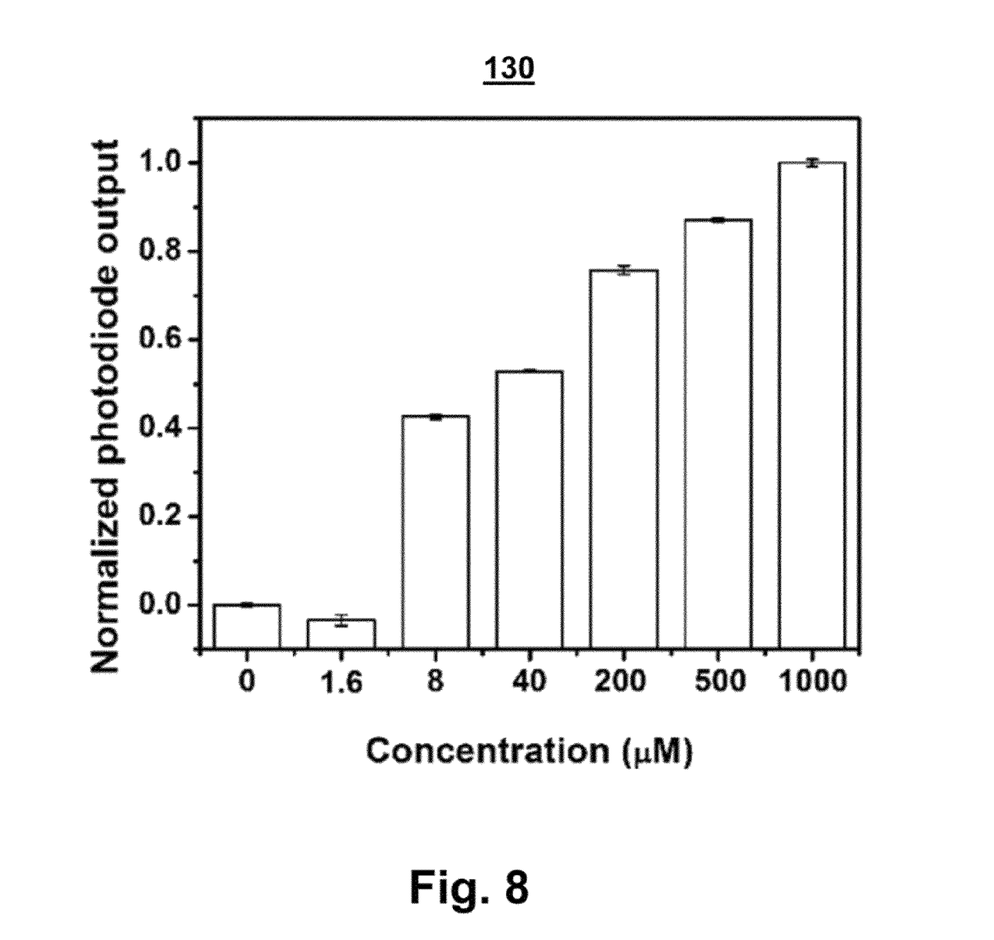
FIG. 8 is a graph illustrating change in fluorescent intensity as a function of different BHBA concentrations in BHBA standard solution.

Serum samples with known BHBA concentration and the fortified milk samples spiked with BHBA standards can be mixed with $NAD^+$-functionalized QDs, for analyzing QD emission intensity by the miniaturized optical sensor assembly 120. FIG. 8 shows a bar graph 130 of normalized output from the optical radiation detector 108 as a function of BHBA concentration in a standard solution. The bar graph 130 demonstrates the fluorescence intensities of the NADH-QDs 24 at 655 nm which are dependent on the concentrations of BHBA. As the concentration of BHBA increases, the fluorescence intensity increases accordingly, as a consequence of the higher amount of NADH-QDs 24 that are converted from $NAD^+$-QDs 20. It has been shown that an $R^2$ value of 0.9511 can be achieved for a linear response region between 8 μM and 1000 μM with a detection limit of 1.6 μM.

Figure 9:
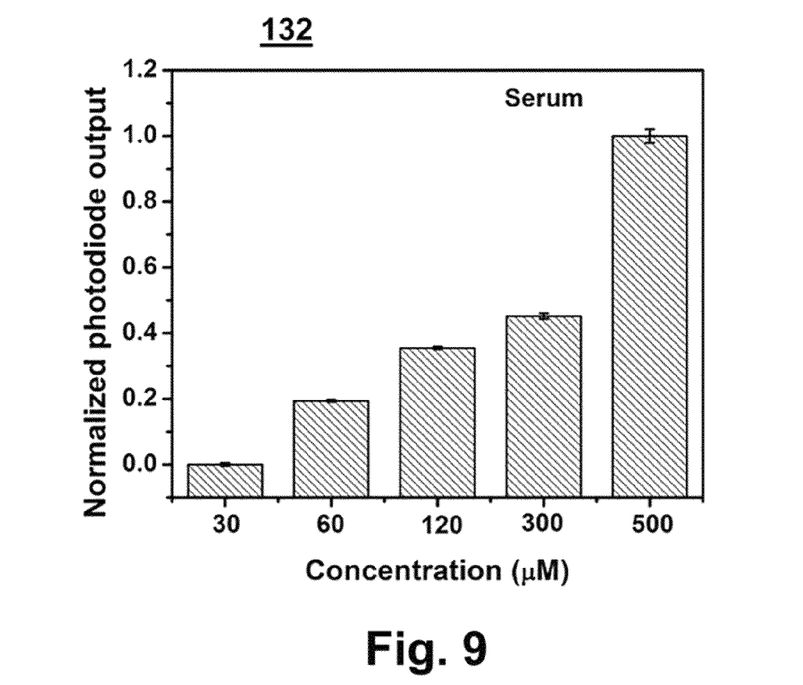
FIG. 9 is a graph illustrating change in fluorescent intensity as a function of different BHBA concentrations in serum samples.
Figure 10:
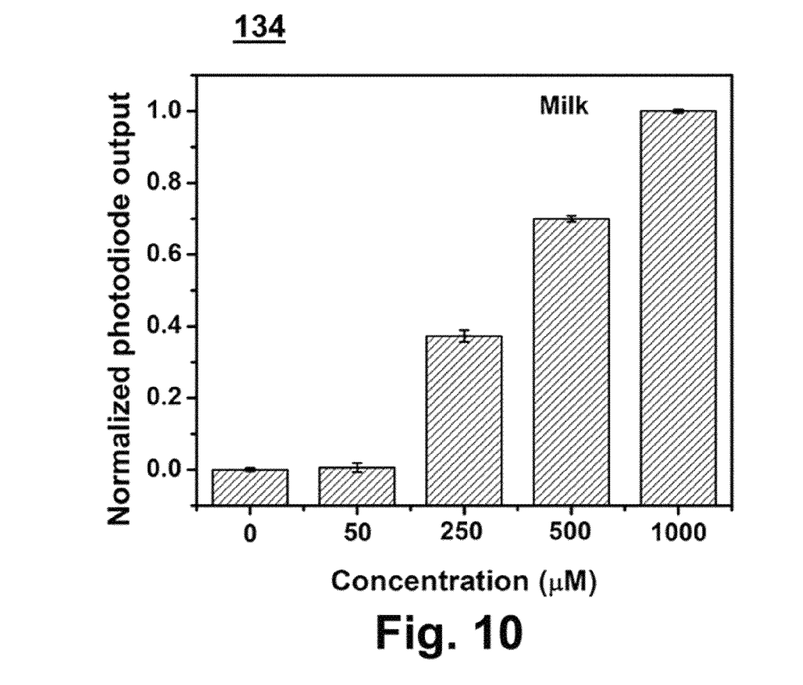
FIG. 10 is a graph illustrating change in fluorescent intensity as a function of different BHBA concentrations in milk samples.

As shown in the bar graph 132 of FIG. 9, different BHBA concentrations in the serum sample are well differentiated, according to the changes of fluorescent intensity values shown on the vertical axis. Similarly, in the bar graph 134 of FIG. 10, different BHBA concentrations in the milk sample are also well differentiated, with fluorescent intensity values shown on the vertical axis. In the milk samples, there is no significant fluorescent signal interference due to complex matrix. The obvious advantage of the disclosed fluorometric method is that no tedious pretreatment is needed to obtain a transparent status for milk. Therefore, contamination and disturbance caused by a precipitating step itself may be avoided. It can be appreciated by one skilled in the art that the disclosed fluorometric determination of BHBA based on $NAD^+$-functionalized QDs 20 is a valid method for analysis of serum or milk.

It is to be understood that the description herein is only exemplary of the invention, and is intended to provide an overview for the understanding of the nature and character of the disclosed SCK detection methods. The accompanying drawings are included to provide a further understanding of various features and embodiments of the method and devices of the invention which, together with their description serve to explain the principles and operation of the invention.

What is claimed is:

1. A method of detecting subclinical ketosis in a dairy animal, said method comprising the steps of:
   obtaining a sample from the dairy animal, said sample containing one of a serum sample or a milk sample;
   incubating a mixture of said sample and a reactant containing $NAD^+$-functionalized quantum dots to produce an incubated mixture;
   irradiating said incubated mixture with optical radiation of a first wavelength so as to emit fluorescent radiation of a second wavelength from said incubated mixture;
   irradiating a photodetector with said fluorescent radiation so as to generate an electrical signal; and
   performing data acquisition using said photodetector electrical signal to determine a β-hydroxybutyrate (BHBA) concentration for the sample.

2. The method of claim 1 further comprising the step of preparing said reactant by modifying a plurality of carboxyl group capped quantum dot nanoparticles with 3-aminophenyl boronic acid (APBA) with a carbodiimide reaction.

3. The method of claim 1 further comprising the step of using a 470 nm single band bandpass filter to optically filter said optical radiation of said first wavelength.

4. The method of claim 1 further comprising the step of using a 655 nm single band bandpass filter to optically filter said optical radiation of said second wavelength.

5. A method of detecting subclinical ketosis using a sample from a dairy animal, said method comprising the steps of:
   preparing a reactant containing $NAD^+$-functionalized quantum dots by modifying a plurality of carboxyl group capped quantum dot nanoparticles with 3-aminophenyl boronic acid (APBA) with a carbodiimide reaction;
   incubating said reactant with the sample to produce an incubated mixture;
   irradiating said incubated mixture with 470 nm optical radiation;
   irradiating a photodetector with fluorescent radiation emitted from said incubated mixture so as to generate an electrical signal; and
   performing data acquisition on said electrical signal to determine a BHBA concentration for the sample.

6. The method of claim 5 further comprising the step of centrifuging the sample at room temperature at 2300 g's for three minutes, prior to said step of incubating.

7. The method of claim 5 further comprising the steps of centrifuging the sample at 2990 g's at 4° C. to harvest serum, and storing at −20° C., prior to said step of incubating.

8. A biosensor system suitable for detecting subclinical ketosis (SCK) in a subject animal from a sample of blood serum or milk obtained from the subject animal, said system comprising:
   a reactant containing a plurality of nicotinamide adenine dinucleotide ($NAD^+$)-functionalized quantum dots;
   a microfluidic chip having a sensing well for receiving an assay mixture of the sample and said reactant;
   an optical sensor assembly having an optical radiation source for inducing fluorescent radiation in said assay mixture, and an optical detector for producing an electrical signal in response to said fluorescent radiation; and
   at least one of a microcontroller board, a computer, and a mobile communication device for receiving said electrical signal and performing data acquisition to determine the amount of β-hydroxybutyrate (BHBA) in the sample.

9. The biosensor system of claim 8 wherein carboxyl group capped quantum dot nanoparticles are modified with 3-aminophenyl boronic acid (APBA) through a carbodiimide reaction to produce said nicotinamide adenine dinucleotide ($NAD^+$)-functionalized quantum dots.

10. The biosensor system of claim 8 wherein said microfluidic chip further comprises a film of solidified PDMS polymer bonded to a glass slide.

11. The biosensor system of claim 8 wherein said microfluidic chip further comprises an incubation region for holding said assay mixture for an incubation process.

12. The biosensor system of claim 8 wherein said optical sensor assembly further comprises a single band bandpass filter disposed between said optical radiation source and said optical detector.

13. The biosensor system of claim 12 wherein said single bandpass filter comprises one of a 470 nm filter and a 655 nm filter.

* * * * *